United States Patent [19]

Wei et al.

[11] Patent Number: 4,461,726

[45] Date of Patent: Jul. 24, 1984

[54] DESULFURIZATION OF PENICILLINS TO PREPARE AZETIDINONES

[75] Inventors: Chung-Chen Wei, Cedar Knoll; Manfred Weigele, North Caldwell, both of N.J.

[73] Assignee: Hoffmann-La Roche Inc., Nutley, N.J.

[21] Appl. No.: 379,386

[22] Filed: May 17, 1982

[51] Int. Cl.$^3$ ................ C07D 205/08; C07D 403/04; C07D 401/12; C07D 403/12
[52] U.S. Cl. ........................... 260/239 A; 260/245.4; 260/330.9; 546/275
[58] Field of Search ............ 260/239 A, 245.4, 330.9; 546/275

[56] References Cited

PUBLICATIONS

Whitesitt et al., Tetrahedral Letters, 1978, 1737.
Duranti et al., *Synthesis*, 1977, p. 494.
Van Heyninger et al., J. Med. Chem., 11, 933, (1968).
Wolfe et al., Chem. Comm., 1970, p. 833.

*Primary Examiner*—Mark L. Berch
*Attorney, Agent, or Firm*—Jon S. Saxe; Bernard S. Leon; Matthew Boxer

[57] ABSTRACT

A process for the Raney nickel desulfurization of penicillins is described. In the process of the invention, amino penicillanic acid or derivatives thereof are reacted with Raney nickel under controlled conditions of temperature and time to yield azetidinones which are useful as intermediates for the synthesis of monocyclic beta-lactam antibiotics.

16 Claims, No Drawings

DESULFURIZATION OF PENICILLINS TO PREPARE AZETIDINONES

SUMMARY OF THE INVENTION

It has long been known that the reaction of penicillins of formula Ia with Raney nickel afford dethiopenicillins of formula IIa, according to the following reaction:

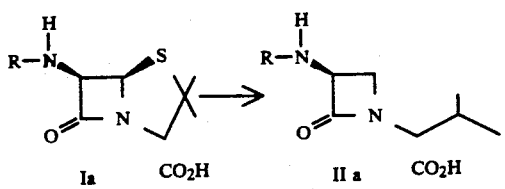

wherein R is as hereinafter described

Examples of this reaction are described in E. Kaczka and K. Folkers, "The Chemistry of Penicillin", Princeton University Press, Princeton, N.J., 1949, p. 243; E. Van Heyningen and L. K. Ahern, *J. Med. Chem.*, 11, 933 (1968); E. Duranti and P. Bonifazi, *Synthesis*, 494 (1977); S. Wolfe and S. K. Hasan, *Chem. Commun.*, 833 (1970); and T. Kamiya, "Recent Advances in the Chemistry of β-Lactam Antibiotics", The Chemical Society, p. 281 (1977).

In contrast to previous literature reports, it has now been found that the desulfurization of penicillins of formula I with Raney nickel, when carried out under the controlled conditions of the invention, affords principally azetidinones of formula III and compounds of formula II as byproducts, according to the following reaction scheme:

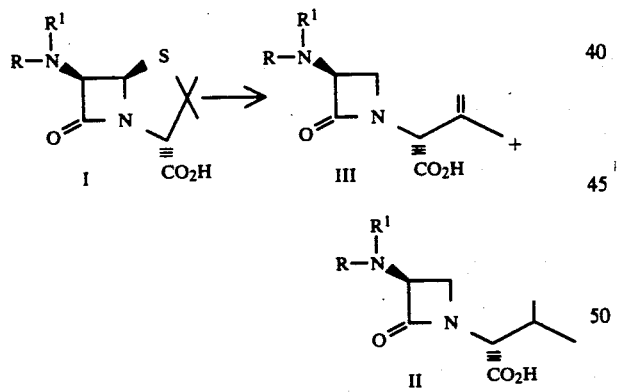

Thus, the present invention is directed to a process for the preparation of compounds of formula III

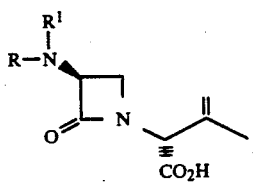

wherein R and $R^1$ taken together are phthaloyl, or $R^1$ is hydrogen and R is hydrogen or a group of the formula

wherein $R^2$ is
(a) hydrogen, lower alkyl, halomethyl or phenyl;
(b) benzyloxy, 4-nitrobenzyloxy, 2,2,2-trichloroethoxy, tert-butoxy or 4-methoxybenzyloxy;
(c) a group of the formula

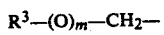

wherein m is 0 or 1; and $R^3$ is 1,4-cyclohexadienyl, phenyl or phenyl substituted with 1 or 2 substituents independently selected from the group consisting of halo, hydroxy, nitro, cyano, trifluoromethyl, $C_1$-$C_7$ alkyl and $C_1$-$C_7$ alkoxy;
(d) a group of the formula

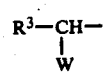

wherein $R^3$ is as defined above; and W is hydroxy, protected hydroxy, carboxy, protected carboxy, amino, or a group of the formula

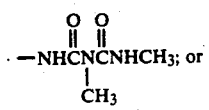

(e) a group of the formula

wherein $R^4$ is a heterocyclic group selected from 2-furyl, 5-tetrazolyl, 1-tetrazolyl, 4-isoxazolyl, or pyridyl,
which comprises reacting a compound of the formula I

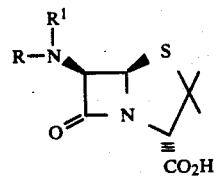

with Raney nickel, when R and $R^1$ are hydrogen, at a temperature in the range of about 60° C. to about 100° C. and a reaction time in the range of from about 15 to about 60 minutes, or when R and/or $R^1$ are other than hydrogen, at a temperature in the range of from about 100° C. to about 200° C. and a reaction time in the range of from about 10 to about 40 minutes, and, in each instance, if desired, separating the resulting compound of formula III by recrystallization or the like. Alternatively, the reaction product of formula III may be utilized in situ.

In the process of the invention, an acid addition salt of the compound of formula I, when R and $R^1$ are hydrogen, can also be utilized.

The nylon blend used in the present invention may be extruded by known methods e.g. through a flat die. When extruded through a flat die the blend film may be monoaxially oriented by a process similar to that disclosed in Canadian Pat. No. 1 011 520 issued June 7, 1977 of I. K. MacGregor.

Preferably, however, the nylon blend may be oriented by a process similar to that disclosed in Applicant's copending patent application Ser. No. 467,823 filed Feb. 18, 1983. Film oriented accordingly has good film flatness, a property of particular importance where the oriented nylon film is to be printed. In the process of Ser. No. 467,823, cast film made from the nylon 66/other nylon blend of the present invention is machine-direction oriented in a narrow-gap orientation process in which the force on each nip roll associated with the orientation rolls is between about 15 and 45 N/cm length of nip roll.

The nylon film of the present invention should be monoaxially oriented at a draw ratio between about 1.1 and 5.5, preferably between about 2.6 and 4.8, especially from 3.0 to 4.2.

Alternatively, the film of the blend may be biaxially oriented by known methods e.g. tenter stretching.

The orientation may be performed at temperatures between 70° C. and 180° C., preferably between 140° C. and 170° C. It is further preferred that the oriented nylon blend film be heat set at a temperature in the range of the orientation temperature and 20° C. below the melting temperature of the blend. Preferably, heat setting should be at a temperature between the orientation temperature and 30° C. below the melting temperature of the blend.

Moisturizing of the film may be accomplished at any time prior to use. However, but it is preferred to moisturize the film between casting and orienting in order to plasticize the film and thus facilitate the orientation process by, for example, lessening the chance of breakage of the film. Moisturizing to the required level is most advantageously accomplished by passing the film, prior to orientation, through a steam chest. Preferably the steam in the steam chest is at a relative humidity of from about 60 to 99% at a temperature of from about 30° to 70° C. The moisture content in the film may be determined by measuring the weight loss of the film after 1 hr. at 105° C.

As indicated hereinabove, film may be moisturized prior to orientation. It is also desirable that the film be moisturized after orientation, and more preferably after being heat set, prior to being wound up on a roll.

In the case where film is extruded, moisturized, not oriented, wound up on a roll and stored for orientation at a subsequent time it may be desirable to remoisturize the film in the subsequent orientation step. Subsequent orientation may take place at any time e.g. 1-2 weeks, after extrusion. In such case the unoriented film may be moisturized prior to winding up on a roll. If the unoriented film is moisturized, the length of time of storage and the dryness of the place of storage may dictate that the film be subjected to a further moisturizing step in the subsequent orientation process in order to bring the moisture content of the oriented film to a level of from 0.75 to 2.25 wt. %.

The residence time of the film in the steam chest is easily determined through simple experimentation. Generally residence times between about 1 and 10 seconds suffice. For example, and oriented film of about 51 μm in thickness would require a residence time of about 2 seconds in a steam chest wherein the steam is at 95% RH (relative humidity) at 45° C., in order to moisturize the film to a level of from about 1 to about 2 wt. %.

Moisturizing the film improves the pinhole resistance of the film and imparts better dimensional stability thereto, e.g. reduces the machine direction shrinkage of the film.

The oriented nylon blend film is advantageously combined with a sealant web. The nylon film provides the required properties of printability, oxygen permeability, clarity, stiffness and dimensional stability, while the sealant web provides a heat sealable layer for heat sealing the edges of packages. This multilayer film may be formed in a number of ways.

One method of making the multilayer film is to extrusion coat the moisturized oriented nylon film with the sealant web by known extrusion coating methods. Sealant webs useful in this process include polyethylenes and ethylene vinyl acetate copolymers.

Another method of making the multilayer film is to laminate the sealant to the moisturized oriented nylon film with a suitable adhesive. One such adhesive is a single component polyurethane adhesive. Such laminating processes are well known in the art.

Preferred sealant webs are films made from linear low density polyethylenes or blends of a linear low density polyethylene with a high pressure polyethylene or an ethylene vinyl acetate copolymer. Preferred linear low density polyethylenes are copolymers of ethylene and $C_4$–$C_{10}$ α-olefins, having a density between 0.915 g/cm$^3$ and 0.945 g/cm$^3$. Particularly preferred are copolymers of ethylene and butene-1, and ethylene and octene-1.

If a multilayer film having a very low oxygen permeability is desired, a layer of crystalline vinylidene chloride copolymer may be placed between the nylon film and the polyethylene film. This may be accomplished in several ways e.g. using a polyurethane primer between the nylon film and the vinylidene chloride copolymer, similar to the method disclosed in Canadian patent 851 140 issued Sept. 8, 1970 to D. G. James, and then laminating e.g. with a polyurethane adhesive, the polyethylene film to the layer of vinylidene chloride copolymer.

Alternatively the vinylidene chloride copolymer may be laid on the nylon film using an amorphous vinylidene chloride copolymer primer and a crystalline vinylidene chloride copolymer, as disclosed in copending patent application No. 408 492.

The present invention provides a film which has good dimensional stability e.g. 2–3% in the machine direction and 0% in the transverse direction, at 149° C.

The following tables shows the benefits of moisturized oriented film of the present invention made from a blend of nylon 66 and nylon 6 compared to nylon 6 and nylon 66 films.

| Nylon Film | Machine Direction Draw Ratio | Modulus (psi) | | TD/MD | Gelbo Flex (pinholes/ 100 in$^2$) | Haze | Elmendorf Tear (g/mil) | |
|---|---|---|---|---|---|---|---|---|
| | | TD | MD | | | | MD | TD |
| Nylon 6 | 4.1 | 338 000 | 278 000 | 1.22 | 45 | 2.7 | 116 | 82 |

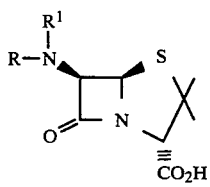

wherein R and R$^1$ are as described above,
are penicillins and are well known in the art and may be prepared according to methods well known in the art such as are reviewed in Flynn, "Cephalosporins and Penicillins", Academic Press, New York and London (1972) pp. 27–91. Of particular note are pages 27–37 which disclose the preparation of 6-amino penicillanic acid by biological methods and pages 39–70 which disclose the preparation of 6-amino penicillanic acid by chemical methods. Also of note are pages 74–91 which disclose acylation of the amino group of 6-amino penicillanic acid to yield acylated moieties corresponding to various naturally-occurring and synthetically-prepared penicillins.

In the process of the present invention, a compound of the formula

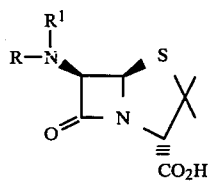

wherein R and R$^1$ are as described above,
is reacted with Raney nickel, when R and R$^1$ are hydrogen, at temperatures in the range of about 60° C. to about 100° C., and a reaction time is in the range of about 15 to about 60 minutes, or when R and/or R$^1$ are other than hydrogen, at a temperature in the range of about 100° C. to about 200° C. and a reaction time in the range of about 10 to about 40 minutes so as to yield a compound of the formula

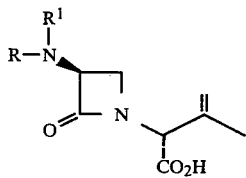

wherein R and R$^1$ are as above.

The reaction, when R and/or R$^1$ in formula I are other than hydrogen, is preferably carried out at temperatures in the range of from about 140° C. to about 180° C., most preferably at a constant temperature of about 165° C. The reaction time, when R and/or R$^1$ in formula I are other than hydrogen, is preferably carried out in the range of from about 15 to about 25 minutes, most preferably about 20 minutes.

In a most preferred embodiment, a compound of the formula

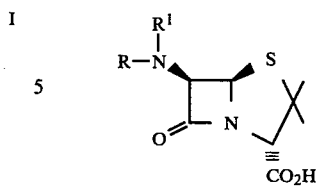

wherein R and R$^1$ are hydrogen, is reacted with Raney nickel at a temperature in the range of about 60° C. to about 100° C., and a reaction time in the range of from about 15 minutes to about 60 minutes.

The reaction, wherein R and R$^1$ in formula I are hydrogen, is preferably carried out at a temperature in the range of about 70° C. to about 85° C., most preferably at a constant temperature of about 75° C. The reaction time is preferably in the range of about 25 to about 35 minutes, most preferably about 30 minutes.

The Raney nickel utilized in the process of the invention is preferably of the W-2, W-4 or Type 28, most preferably of the type prepared according to Example 4 of the present invention. Furthermore, the reaction may be carried out in any polar solvent, preferably in aqueous solution.

The examples which follow further illustrate the invention. All temperatures are in degrees centigrade unless otherwise stated.

EXAMPLE 1

Desulfurization of Sodium 6-Aminopenicillanate with Raney Nickel Catalyst

A solution of 6-aminopenicillanic acid (64.8 g, 0.3 mol) and sodium bicarbonate (25.9 g, 0.3 mol) in water (750 ml) was poured into a well-stirred suspension of Raney nickel prepared as described in Example 4 (650 g) in water (1,350 ml) and placed in a preheated bath (76°) with vigorous stirring for 35 minutes. The reaction mixture was then cooled immediately, filtered and washed with a small amount of water. To the combined filtrate was added sodium bicarbonate (51.8 g, 0.62 mol) and benzyl chloroformate (60 ml, 0.42 mol) in acetone (60 ml). The resulting mixture was stirred vigorously for 3 hours. The reaction mixture, after washing with dichloromethane (3×750 ml), was acidified to pH 3 with concentrated hydrochloric acid at 0° C. and stirred at room temperature for 1 hour. Filtration of the solid gave 30.2 g (31%) of the mixture of [1R, 3S]-alpha-(1-methylethenyl)-2-oxo-3-amino-1-azetidineacetic acid and [1R, 3S]-alpha-(1-methylethenyl)-2-oxo-3-amino-1-azetidineacetic acid as N-carbobenzoxy derivative. Based on the nmr signals (CDCl$_3$) at 2.0 and 1.2 ppm, the crude product contained [1R, 3S]-alpha-(1-methylethyl)-2-oxo-3-amino-1-azetidineacetic acid and [1R, 3S]-alpha-(1-methylethenyl)-2-oxo-3-amino-1-azetidineacetic acid in a one-to-one ratio. The mixture crystallized from methyl alcohol-water and repeated recrystallization from chloroform gave the N-carbobenzoxy derivative of [1R, 3S]-alpha-(1-methylethenyl)-2-oxo-3-amino-1-azetidineacetic acid in 97% purity, mp 151°–152°.

C$_{16}$H$_{18}$N$_2$O$_5$: Calculated: C, 60.37; H, 5.70; N, 8.80. Found: C, 60.10; H, 5,81; N, 8.80.

EXAMPLE 2

Desulfurization of Potassium 6-Phenylacetamidopenicillanate with Raney Nickel To a solution of potassium 6-phenylacetylaminopenicillanate (11.5 g, 0.03 mol) in water (600 ml) was added Raney nickel prepared as described in Example 4 (72 g), and the mixture was placed in a preheated oil bath (165°) with vigorous stirring for 15 minutes. The reaction was then cooled immediately, filtered and washed with water. The combined filtrates were acidified to pH 2 with concentrated hydrochloric acid and extracted with ethyl acetate (3×200 ml). The extract was washed with water, dried over sodium sulfate and evaporated in vacuo to give 6.4 g of an oil; tlc [silica]; ethylacetate:acetic acid:water, 60:3:1; two major spots with $R_f$ 0.31 ([1R,3S]-alpha-(1-methylethyl)-2-oxo-3-[phenylacetyl-amino]-1-azetidineacetic acid) and 0.18 ([1R,3S]-alpha-(1-methylethenyl)-2-oxo-3-[phenylacetylamino]-1-azetidineacetic acid)].

To the mixture of [1R,3S]-alpha-(1-methylethyl)-2-oxo-3-[phenylacetylamino]-1-azetidineacetic acid and [1R,3S]-alpha-(1-methylethenyl)-2-oxo-3-[phenylacetylamino]-1-azetidineacetic acid in dichloromethane (60 ml), a solution of diphenyldiazomethane in dichloromethane was added portionwise until the purple color persisted and stirred for 3 hours at room temperature. The excess of diphenyldiazomethane was then decomposed with acetic acid, and the organic solutions were washed with 5% sodium bicarbonate, water, dried over sodium sulfate and evaporated to dryness. The oily residue obtained was purified on preparative High-performance liquid chromatography [silica, ethyl acetate-hexane, 1:1; $R_f$ 0.14] and crystallized from ethyl acetate-hexane (1:1) to give 5.2 g (35%) of the inseparable benzhydryl esters of [1R,3S]-alpha-(1-methylethyl)-2-oxo-3-]phenylacetyl-amino]-1-azetidineacetic acid and [1R,3S]-alpha-(1-methylethenyl)-2-oxo-3-[phenylacetyl-amino]-1-azetidineacetic acid in 6 to 4 ratio based on the nmr analysis. These esters can be used directly for subsequent reactions such as isomerization, epoxidation or bromination to give the separate mixture of products and the unreacted benzhydryl ester of [1R,3S]-alpha-(1-methylethyl)-2-oxo-3-[phenylacetylamino]-1-azetidineacetic acid.

EXAMPLE 3

Desulfurization of Potassium 6-Phenoxyacetamidopenicillanate with Raney Nickel The desulfurization method described for potassium 6-phenylacetylpenicillanate was followed. Thus, 5.7 g (38%) of the inseparable benzhydryl esters of [1-R,3S]-alpha-(1-methylethyl)-2-oxo-3-[phenoxyacetylamino]-1-azetidineacetic acid and [1-R,3S]-alpha-(1-methylethenyl)-2-oxo-3-[phenoxyacetylamino]-1-azetidineacetic acid in the ratio of 6.4 to 3.6, respectively (silica; ethylacetate:Hexane, 1:1; $R_f$ 0.22) was obtained from potassium 6-phenoxyacetylaminopenicillanate (12.03 g, 0.03 mol) and Raney nickel prepared as described in Example 4 (72 g).

EXAMPLE 4

Preparation of Raney Nickel 120 gallons of water was metered into a 500-gallon kettle. The water was agitated, and over approximately 10 minutes, 63 gallons (400 lbs as 100% NaOH) of caustic soda, 50%, were metered in. The temperature rose to about 70° C. during the caustic soda addition. When necessary, steam may be applied to heat contents of kettle to 70° C.

With a scoop, 400 lbs. of nickel aluminum alloy which consists of aluminum 49.9%, nickel 49.9% and iron 0.43% was slowly sprinkled into a kettle. The powder was added slowly to minimize foaming and to maintain the temperature at a maximum of 100° C. A small stream of water may also be added to the kettle to help control the temperature and maintain volume during the nickel aluminum alloy addition. The nickel aluminum alloy muxt be added over a one and one half to two-hour period. During the addition of the nickel aluminum alloy, it may be necessary to balance the stream of water flow and the steam to the jacket in order to maintain the temperature and not to exceed 100° C.

The jacket steam pressure was adjusted to 25-30 psig and heated to 110° C. The temperature was maintained at 110° C. for one hour. This hold time is critical to the formation of the desired catalyst. Extending or shortening this one-hour digestion period may lead to formation of an undesirable type of catalyst.

The jacket steam pressure was increased to 55-60 psig, and the water was evaporated over about a one hour period. The batch temperature reached approximately 125°-130° C. over this one hour period.

The reaction mixture was quenched by metering 150 gallons of filtered city water into a kettle. The reaction was agitated for 10 minutes. The agitator was turned off, and the Raney nickel catalyst was allowed to settle for 15 minutes. A steam syphon system was used to separate the supernatant liquid through the 55-gallon steel drum trap number 2 into the sewer. While making the separation, the pH should be taken with hydrion paper at the drum trap and recorded on a log sheet, pH will be initially over 13.

The above step was repeated three times with 150 gallons of filtered city water. The total volume of wash water was 600 gallons.

Approximately 50% of the fresh Raney nickel catalyst was transferred via the steam syphon into the 55-gallon wash tank. An air motor was attached to the wash tank, and the agitator was started slowly to prevent the catalyst from overflowing. The filtered city water was turned on and the water flow rate adjusted to a rotometer reading of 110-120 mm, and the Raney nickel catalyst was washed continuously until the effluent was clear and the ph was between 9 and 10. The effluent from the wash tank through the drum trap number 1 should be checked at hourly intervals with hydrion paper and the pH recorded on a log sheet.

The air motor was removed from the wash tank, and the catalyst was allowed to settle for 30 minutes. Using the steam syphon system, the supernatant liquid was separated off into drum trap number 2. The wash tank was tilted into the horizontal position, and the catalyst was poured into a tared 20-gallon pot. All the catalyst fit into one pot.

The excess water from the 20-gallon pot was ladled. The wet catalyst in the 20-gallon pot was weighed, and the gross, tare and net weights were recorded on the log sheet. Sufficient water to cover the catalyst was added. The portion of the procedure beginning with the transfer of 50% of the fresh Raney nickel to the steam syphon through the addition of sufficient water to cover the catalyst was repeated with the remaining 50% of the fresh Raney nickel in the kettle.

Once a week, the contents of drum traps numbers 1 and 2 were ladled into a tared pot, and the excess water was removed. The gross, tare and net weight of the pot was measured and recorded. Net weight and batch numbers of catalyst prepared during this period were recorded in the sludge recovery book.

EXAMPLE 5

Synthesis of 3-Carbobenzyloxyamino-2-Azetidinone 30 g (0.073 mol) of a mixture of ([1R,3S]-alpha-(1-methylethyl)-2-oxo-3L-carbobenzyloxyamino-1-azetidineacetic acid benzyl ester and [1R, 3S]-alpha-(1-methylethenyl)-2-oxo-3-carbobenzyloxyamino-1-azetidineacetic acid benzyl ester in 600 ml of dichloromethane and 17 ml of triethylamine was refluxed (oil bath 80° C. or steam bath) for 5 hours. The methylene chloride solution was washed successively with 1N hydrochloric acid, water, 5% sodium bicarbonate, water and dried over sodium sulfate. Removal of the solvent in vacuo gave 30 g of oil which was used for the next step without further purification.

22 g (0.054 mol) of the azetidinones obtained from the foregoing step in 120 of acetone and 3.77 g (0.021 mol) of potassium dihydrogen phosphate in 40 ml of water was stirred and cooled to −3° C. To this vigorously-stirred solution was added 4.28 g (0.027 mol) of potassium permanganate (pulverized in mortar) over a 10-minute period so that the temperature remained below 0° C. After complete addition, the reaction mixture was stirred at 0° C. for 30 minutes. Then added 0.7 g (0.006 mol) of sodium bisulfite in 10 ml of water, and the reaction was stirred for 10 minutes. To this mixture was added 200 ml of 1N sodium carbonate and 300 ml of dichloromethane and stirred at 0° C. for 30 minutes. After the separation of dichloromethane layer, the reaction was further extracted two times with 150 ml of dichloromethane. The combined methylene chloride extract was filtered through Celite, and the filtrate was washed with water and dried over sodium sulfate. Removal of the solvent gave 21 g of oil which was crystallized from 50 ml of ethyl acetate. After cooling at 0° C. overnight, the crystal was filtered and washed three times with 4 ml of cold ethyl acetate to give 1.56 g (33%) of 3-carbobenzyloxyamino-2-azetidinone. The mother liquor was stripped to dryness to give 15 g of oil which was crystallized from 120 ml of ethyl acetate-pet. ether (3:7) to give 8.6 g (65%) of the unreacted [1R, 3S]-alpha-(1-methylethyl)-2-oxo-3-carbobenzyloxyamino-1-azetidinecetic acid benzyl ester.

What is claimed is:

1. A process for the preparation of a compound of the formula

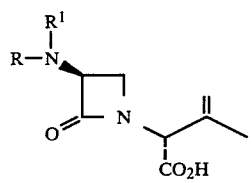

III wherein R and $R^1$, taken together, are phthaloyl, or $R^1$ is hydrogen and R is hydrogen or a group of the formula

wherein $R^2$ is
(a) hydrogen, lower alkyl, halomethyl or phenyl;
(b) benzyloxy, 4-nitrobenzyloxy, 2,2,2-trichloroethoxy, tert-butoxy or 4-methoxybenzyloxy;
(c) a group of the formula

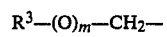

wherein m is 0 or 1, and $R^3$ is 1,4-cyclohexadienyl, phenyl or phenyl substituted with 1 or 2 substituents independently selected from the group consisting of halo, hydroxy, nitro, cyano, trifluoromethyl, $C_1$-$C_7$ alkyl and $C_1$-$C_7$ alkoxy;
(d) a group of the formula

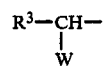

wherein $R^3$ is 1,4-cyclohexadienyl, phenyl or phenyl substituted with 1 or 2 substituents independently selected from the group consisting of halo, hydroxy, nitro, cyano, trifluoromethyl, $C_1$-$C_7$ alkyl and $C_1$-$C_7$ alkoxy, and W is hydroxy, carboxy, formyloxy, chloroacetoxy, benzyloxy, benzhydryloxy, trityloxy, 4-nitrobenzyloxy, trimethylsilyloxy, tert-butoxy, methoxymethoxy, tetrahydropyranyloxy, tert-butoxycarbonyl, 4-nitrobenzyloxycarbonyl, 2,2,2-trichloroethoxycarbonyl, amino, tert-butoxycarbonylamino, benzyloxycarbonylamino, 4-methoxybenzyloxycarbonylamino, 4-nitrobenzyloxycarbonylamino, 2,2,2-trichloroethoxycarbonylamino, 1-carbomethoxy-2-propenylamino, or a group of the formula

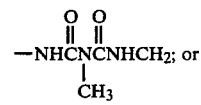

(e) a group of the formula

wherein $R^4$ is 2-furyl, 5-tetrazolyl, 1-tetrazolyl, 4-isoxazolyl, or pyridyl, or when R is hydrogen, a hydrochloride acid addition salt thereof,
which comprises reacting a corresponding compound of the formula

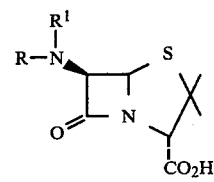

with Raney nickel, when R and $R^1$ are hydrogen, at a temperature in the range of from about 60° C. to about 100° C. for a period of time in the range of from about 15 to about 60 minutes or, when R and/or $R^1$ are other than hydrogen, at a reaction temperature in the range of from about 100° C. to about 200° C. for a period of time in the range of from about 10 to about 40 minutes and wherein said Raney nickel is prepared by reacting a nickel aluminum iron alloy in powder form with an aqueous solution of NaOH at 110° C. for one hour.

2. A process according to claim 1, wherein R and $R^1$ are hydrogen.

3. A process according to claim 1, wherein $R^1$ is hydrogen and R is a group of the formula $$R^2-\overset{O}{\underset{\|}{C}}-$$

wherein $R^2$ is hydrogen, lower alkyl, halomethyl or phenyl.

4. A process according to claim 1, wherein $R^1$ is hydrogen and R is a group of the formula $$R^2-\overset{O}{\underset{\|}{C}}-$$

wherein $R^2$ is benzyloxy, 4-nitrobenzyloxy, 2,2,2-trichloroethoxy, tert-butoxy or 4-methoxybenzyloxy.

5. A process according to claim 1, wherein $R^1$ is hydrogen and R is a group of the formula $$R^2-\overset{O}{\underset{\|}{C}}-$$

wherein $R^2$ is a group of the formula $$R^3-(O)_m-CH_2-$$

wherein m is 0 or 1 and $R^3$ is 1,4-cyclohexadienyl, phenyl or phenyl substituted with 1 or 2 substituents independently selected from the group consisting of halo, hydroxy, nitro, cyano, trifluoromethyl, $C_1-C_7$ alkyl and $C_1-C_7$ alkoxy.

6. A process according to claim 1, wherein $R^1$ is hydrogen and R is a group of the formula $$R^2-\overset{O}{\underset{\|}{C}}-$$

wherein $R^2$ is a group of the formula $$R^3-\underset{W}{\underset{|}{CH}}-$$

wherein $R^3$ is 1,4-cyclohexadienyl, phenyl or phenyl substituted with 1 or 2 substituents independently selected from the group consisting of halo, hydroxy, nitro, cyano, trifluoromethyl, $C_1-C_7$ alkyl and $C_1-C_7$ alkoxy, and W is hydroxy, carboxy, formyloxy, chloroacetoxy, benzyloxy, benzhydryloxy, trityloxy, 4-nitrobenzyloxy, trimethylsilyloxy, tert-butoxy, methoxymethoxy, tetrahydropyranyloxy, tert-butoxycarbonyl, 4-nitrobenzyloxycarbonyl, 2,2,2-trichloroethoxycarbonyl, amino, tert-butoxycarbonylamino, benzyloxycarbonylamino, 4-methoxybenzyloxycarbonylamino, 4-nitrobenzyloxycarbonylamino, 2,2,2-trichloroethoxycarbonylamino, 1-carbomethoxy-2-propenylamino or a group of the formula $$-NH\overset{O}{\underset{\|}{C}}\underset{\underset{CH_3}{|}}{N}\overset{O}{\underset{\|}{C}}NHCH_3.$$

7. A process according to claim 1, wherein R and $R^1$ taken together are phthaloyl.

8. A process according to claim 2, wherein the reaction is carried out at a temperature in the range of from about 60° C. to about 100° C., and a reaction time in the range of from about 15 to 60 minutes.

9. A process according to claim 7, wherein the reaction is carried out at a temperature in the range of from about 70° C. to about 85° C. and a reaction time in the range of about 25 to about 35 minutes.

10. A process according to claim 8, wherein the reaction is carried out a constant temperature of about 75° C. and a reaction time of about 30 minutes.

11. A process according to claim 3, 4, 5, 6 or 7 wherein the reaction is carried out at a temperature in the range of from about 100° C. to about 200° C., and a reaction time in the range of from about 10 to about 40 minutes.

12. A process according to claim 3, 4, 5, 6 or 7 wherein the reaction is carried out at a temperature in the range of from about 140° C. to about 180° C. and a reaction time in the range of from about 15 to about 25 minutes.

13. A process according to claim 3, 4, 5, 6 or 7 wherein the reaction is carried out at a constant temperature of about 165° C., and a reaction time of about 20 minutes.

14. A process according to claim 1 for the preparation of a compound of the formula

III wherein $R^1$ is hydrogen and R is hydrogen or a group of the formula $$Ph-CH_2-\overset{O}{\underset{\|}{C}}-$$

or $$Ph-O-CH_2\overset{O}{\underset{\|}{C}}-$$

which comprises reacting a corresponding compound of the formula with Raney nickel, when R and R¹ are hydrogen, at a temperature in the range of from about 60° C. to about 100° C. for a period of time in the range of from about 15 to about 60 minutes or, when R is other than hydrogen, at a reaction temperature in the range from about 100° C. for a period of time in the range of from about 10 to about 40 minutes and wherein said Raney nickel is prepared by reacting a nickel aluminum iron alloy in powder form with an aqueous solution of NaOH at 110° C. for one hour.

15. A process according to claim 14 wherein R¹ is hydrogen and R is

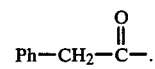

16. A process according to claim 14 wherein R¹ is hydrogen and R is

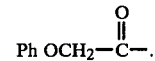

* * * * *